United States Patent
Hoernig

(10) Patent No.: US 8,965,092 B2
(45) Date of Patent: Feb. 24, 2015

(54) METHOD AND APPARATUS TO DETERMINE ACQUISITION PARAMETERS IN DUAL-ENERGY TOMOSYNTHESIS

(71) Applicant: Mathias Hoernig, Erlangen (DE)

(72) Inventor: Mathias Hoernig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 58 days.

(21) Appl. No.: 13/684,780

(22) Filed: Nov. 26, 2012

(65) Prior Publication Data

US 2013/0136331 A1 May 30, 2013

(30) Foreign Application Priority Data

Nov. 25, 2011 (DE) .......................... 10 2011 087 127

(51) Int. Cl.
 *G06K 9/00* (2006.01)
 *G06K 9/78* (2006.01)
 *A61B 6/00* (2006.01)
 *A61B 6/02* (2006.01)
 *A61B 6/04* (2006.01)

(52) U.S. Cl.
 CPC ... *G06K 9/78* (2013.01); *A61B 6/52* (2013.01); *A61B 6/025* (2013.01); *A61B 6/0414* (2013.01); *A61B 6/4452* (2013.01); *A61B 6/481* (2013.01); *A61B 6/482* (2013.01); *A61B 6/502* (2013.01); *A61B 6/5205* (2013.01); *A61B 6/542* (2013.01); *A61B 6/545* (2013.01)
 USPC ......... 382/131; 378/5; 378/9; 378/16; 378/37

(58) Field of Classification Search
 USPC .................... 382/131; 378/5, 9, 16, 37, 98.9
 See application file for complete search history.

(56) References Cited

U.S. PATENT DOCUMENTS

| | | | | |
|---|---|---|---|---|
| 4,649,558 A * | 3/1987 | Brunn et al. | ..................... | 378/97 |
| 6,683,934 B1 * | 1/2004 | Zhao et al. | ......................... | 378/9 |
| 7,352,885 B2 * | 4/2008 | Eberhard et al. | .............. | 382/131 |
| 7,453,983 B2 * | 11/2008 | Schildkraut et al. | ............ | 378/65 |
| 7,734,076 B2 * | 6/2010 | Du et al. | ........................ | 382/128 |
| 7,813,471 B2 * | 10/2010 | Hirokawa et al. | .................. | 378/4 |
| 8,199,874 B2 * | 6/2012 | Toth et al. | ........................ | 378/16 |
| 8,340,380 B2 * | 12/2012 | Morita | ........................... | 382/128 |
| 8,582,857 B2 * | 11/2013 | Chen et al. | .................... | 382/131 |
| 2005/0002550 A1 | 1/2005 | Jabri et al. | | |
| 2006/0269040 A1 * | 11/2006 | Mertelmeier | ................... | 378/37 |
| 2007/0237288 A1 * | 10/2007 | Tkaczyk et al. | ................... | 378/5 |
| 2011/0037761 A1 * | 2/2011 | Mistretta et al. | .............. | 345/419 |
| 2011/0058720 A1 * | 3/2011 | Lu et al. | ........................ | 382/131 |
| 2012/0238870 A1 * | 9/2012 | Smith et al. | ................... | 600/431 |

OTHER PUBLICATIONS

"Die Digitale Mehrschicht-tomographie: erste klinische Ergebnisse," Dü ber et al., Electromedica, vol. 57 (1989), pp. 36-39.

* cited by examiner

*Primary Examiner* — Katrina Fujita
(74) *Attorney, Agent, or Firm* — Schiff Hardin LLP

(57) ABSTRACT

In a control method and a control unit to control a high-energy, tomosynthesis scan in a contrast agent-assisted dual-energy tomosynthesis, image data of a first tomosynthesis scan are evaluated in order to determine the respective grey-scale values for all volume segments. A tube current-time product value for every greyscale value is stored in a memory. For every projection angle, a calculation unit can thereupon calculate a tube current-time product value and acquisition parameters and result with which the second high-energy tomosynthesis scan is controlled.

9 Claims, 4 Drawing Sheets

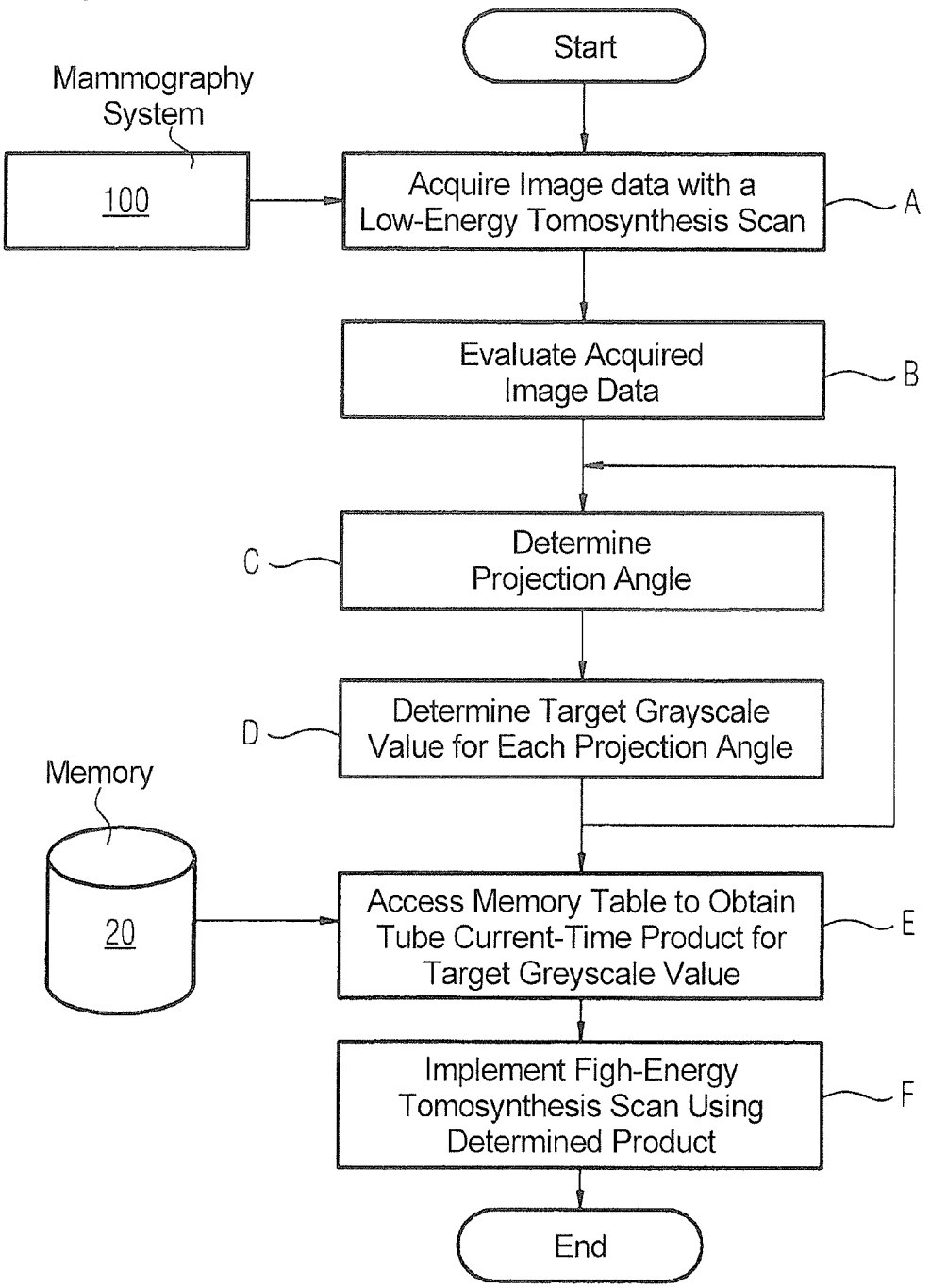

METHOD AND APPARATUS TO DETERMINE ACQUISITION PARAMETERS IN DUAL-ENERGY TOMOSYNTHESIS

BACKGROUND OF THE INVENTION

1. Field of the Invention

The present invention concerns the field of microelectronics and in particular concerns a control unit to control a dual-energy tomosynthesis.

2. Description of the Prior Art

Contrast agent-assisted dual-energy tomosynthesis (CEDET) is a recently developed method in mammography. In such dual-energy imaging, low-energy images are initially acquired without application of contrast agent, and high-energy x-ray images are subsequently generated after a contrast agent injection. This is followed by a calculation method in which the high-energy x-ray images are subtracted with weighting from the low-energy x-ray images. The goal is to be able to better detect specific tissue structures (for example tumor tissue or micro-calcifications). The physical bases for a tomosynthesis method are described (among other things) by Bittner U., Düber C., Koch R., et al. in "Digital Multilayer Tomographie: A New Method of Implementing Classical Serioscopy", Electromedica, 1989; 57:36. In tomosynthesis, a number of projection exposures are acquired from different angles or directions. A data volume of the subject to be examined (normally the female breast, but the present application is not limited to this usage) is subsequently reconstructed from the image data sets obtained in such a manner. The advantage of the method is that such tissue slices can be better acquired the deeper that they are located in the examination subject and/or the more that they are overlaid by denser tissue structures (for example fat tissue).

An improvement of the tomosynthesis method is apparent in contrast agent-assisted tomosynthesis. Before execution of the high-energy x-ray images of the patient, a contrast agent (normally iodine) is administered intravenously before the breast is irradiated. The high-energy acquisitions (which are normally obtained with an energy level above 33 kV) serve to cause visualization of the contrast agent enrichment in tissue and its progression over time. Malignant tumor tissue has a different contrast agent progression (enhancement) with respect to time than benign tissue; the presence of tumor tissue can be concluded based on the contrast agent presentation.

In digital dual-energy subtraction tomosynthesis, image data sets from a first, low-energy x-ray radioscopy are recombined with image data sets from a second, high-energy x-ray radioscopy (after contrast agent injection) in order to obtain a subtraction image. In the recombined subtraction exposure, the tissue in which the contrast agent has enriched in an intensified manner can be shown with emphasis.

This method basically assumes that the patient must be subjected to a double x-ray radioscopy during an examination (in which the breast is compressed and remains statically positioned): a radioscopy to acquire low-energy x-ray images (in order to be able to depict morphological structures of the examination subject), and a radioscopy to acquire high-energy x-ray images (in which the contrast agent enrichment can be shown). Since in this method the patient is exposed to a doubled radiation dose, there exists a basic need to minimize the radiation exposure for the patient as much as possible. Furthermore, it is significant to optimize the quality of the reconstructed image data in order to be able to ensure an improved sensitivity and specificity, so as to be able to ensure a better finding result.

In conventional CEDET methods, it is a disadvantage that the acquisition parameters cannot be configured to execute the second tomosynthesis scan with . high energy level. In particular, this second scan cannot be adapted to examination-specific and patient-specific conditions (such as breast density, tissue composition etc.) that can be derived from the image data of the first tomosynthesis scan. In the conventional methods, this disadvantage has led to suboptimal image results.

SUMMARY OF THE INVENTION

An object of the present invention is to improve the image quality in dual-energy tomosynthesis, while keeping the radiation exposure for the patient as low as possible. Furthermore, it should be possible to adapt the parameters for execution of the x-ray radioscopy to the respective examination subject.

The invention is described in the following using the solution related to the apparatus. Advantages, features or advantageous alternative embodiments that are mentioned herein are also applicable to a control method and to a non-transitory, computer-readable data storage medium according to the invention. The functional aspects of the method are thereby implemented as microprocessor units (hardware units) that execute or have the respective functionality. The mentioned units or modules can likewise also be components of an embedded system that is integrated into the mammography system or into a reconstruction computer and can be used to control the tomosynthesis. In particular, the features described in connection with the control unit are thus likewise to be applicable to the other Claim forms (method and computer program product).

The invention concerns a control unit to control a high-energy tomosynthesis scan within the scope of a dual-energy tomosynthesis of an examination subject (in particular the female breast), that includes the following components.

An acquisition unit is designed to acquire the image data that have been acquired by means of at least one low-energy tomosynthesis scan. In the simplest case, it can be an interface of the control unit to import image data sets (from a buffer [cache] or directly from the imaging modality)

An evaluation unit that is designed to evaluate the acquired image data in order to determine a greyscale value for each volume segment of the examination subject.

A determination unit serves to determine at least one respective corresponding projection angle at which the low-energy tomosynthesis scan has been executed, and a subsequent high-energy tomosynthesis scan should be executed.

A calculation unit is designed to calculate a target greyscale value for the high-energy tomosynthesis scan for each determined projection angle, with all determined greyscale values of the low-energy tomosynthesis scan of those volume segments that fall within the radiation region of the respective projection angle being taken into account in the calculation of the target greyscale value.

A memory is provided in which an association table is stored, wherein a tube current-time product value and/or a high voltage value for execution of the high-energy tomosynthesis scan is/are stored in the association table for each greyscale value or for each target greyscale value.

The control unit is designed to individually control the high-energy tomosynthesis scan with values imported from the memory for the tube current-time product and/or for the high voltage for each respective defined projection angle.

The tomosynthesis is preferably a contrast agent-assisted dual-energy tomosynthesis that is also known as two-spectra tomosynthesis. However, the injection of a contrast agent can alternatively be foregone. The tomosynthesis is based on two x-ray acquisition processes: a low-energy tomosynthesis scan and—after contrast agent injection—a high-energy tomosynthesis scan. Iodine is typically used as a contrast agent, but other contrast agents can be used. The tomosynthesis scans are typically executed in an angle range of, for example, +/−25°. It is also possible to limit the angle range further around a central beam (0°) and to execute only an angle range of +/−10° in order to expose a specific tissue region (region of interest—ROI). The angle range can likewise also be expanded. For the low-energy acquisitions, x-ray tube voltages are advantageously worked with that lie in a range from approximately 23 to 35 $kV_p$ (kilovolt). These high voltage values serve to be able to depict structures of the female breast with glandular tissue, connective tissue, adipose tissue, skin and subcutaneous fat tissue.

Typically a second, high-energy tomosynthesis scan is executed following the first, low-energy tomosynthesis scan. This second, high-energy scan serves to acquire the contrast agent kinetics. A contrast agent injection typically occurs before the first tomosynthesis scan and second tomosynthesis scan. Alternatively, however, here as well as deviating order can be selected so that—for example—the contrast agent injection is executed at a later point in time before the second tomosynthesis scan.

An image volume data set is reconstructed from the image data that were acquired by means of the low-energy tomosynthesis scan and/or by means of the high-energy tomosynthesis scan. In other words: an image volume data set is acquired based on both the low-energy tomosynthesis scan and the high-energy tomosynthesis scan.

The image data set that has been acquired based on the first low-energy tomosynthesis scan by the acquisition unit is initially supplied to the evaluation unit in order to evaluate the image data of the first low-energy scan that are acquired in this manner. The volume of the examination subject that is to be examined is accompanied into individual projection slices. Each projection slice in turn is composed of a number of volume segments. The evaluation unit is designed in order to determine a greyscale value for each volume segment. Moreover, it is possible to create a density profile or a greyscale value profile for all volume segments of the examination subject. The size of a volume segment can be dynamically adapted and can initially cover a larger volume region (that is then iteratively reduced) so that the evaluation unit can provide an evaluation result as quickly as possible. Iteratively, the size of the volume segments can thus be reduced in order to be able to create a more finely granulated greyscale value profile.

In a preferred embodiment, the control unit is provided as an embedded system. The functionality of the control unit can be provided as firmware. The corresponding commands and instructions can be stored in a flash memory, in particular in an EPROM, EEPROM, or in a ROM. The control unit is typically embedded in a mammography system. Alternatively, the control unit can also be activated as a separate instance of the mammography system via a corresponding interface. It is likewise possible to provide the control unit in a reconstruction computer.

In a preferred embodiment, the control unit includes the acquisition unit, the evaluation unit, the determination unit, the calculation unit, and the memory. These units are typically designed as separate microprocessor modules or, according to an alternative embodiment, as separate software modules. In alternative embodiments they can be assembled into a superordinate unit. It is likewise possible for these units to be distributed to different modules. The units can be engaged in a data exchange via a bus system or an interface. In the software-based solution, the aforementioned units can be engaged in a data exchange with one another via a data bus as a distributed system.

The determination unit serves to determine at least one acquisition angle or projection angle at which the subsequent high-energy tomosynthesis scan should be executed. The acquisition angle can either be entered as an input manually by a user or configured automatically. It is likewise possible for the projection angle to be pre-configured. The pre-configuration can be adapted to the angle specifications of the low-energy tomosynthesis scan. For example, the same scan direction can be selected as in the low-energy scan, or an opposite scan direction at essentially the same acquisition angles as in the low-energy scan.

The calculation unit serves to calculate a target greyscale value for a specific projection angle. All determined greyscale values of those volume segments that fall into the radiation region of the specific projection angle are taken into account. In other words, all determined greyscale values of those volume segments that are located within the respective radiation angle are selected. According to a variant of the invention, these determined greyscale values of the selected volume segments can be compared with a signal target value and can be set in linear correlation. It is likewise possible for the target greyscale value to be determined so as to cause a constant contrast/noise ratio (CNR) to exist in relation to the respective image data signals, thus for example the contrast/noise ratio of the contrast agent iodine to the (tissue) background (parenchyma). The target greyscale value can likewise be determined so that a constant signal average is achieved.

In another embodiment of the invention, the units can be assembled into a more comprehensive module. For example, it is thus possible for the evaluation unit, the determination unit and/or the calculation unit to be assembled into one module. It is also possible to omit the determination unit and to design the control unit without the determination unit, and to transfer the functionality of the determination unit (namely the iteration over the respective projection angle at which the high-energy scan should be executed) into the calculation unit. The evaluation unit can likewise be integrated into the calculation unit or into other modules. In a compact version of the invention, the acquisition unit is designed to import the image data via an interface, and the evaluation, determination and/or calculation unit are integrated, as an assembled, more complex calculation unit, directly into the control unit.

An association table is stored in the memory, in which association table is/are stored a tube current-time product value and/or a high voltage value for every greyscale value and/or every target greyscale value. The association table can be implemented in the form of a lookup table or a mapping rule. At least one tube current-time product value is stored with regard to a respective greyscale value. This is usually in units of "mAs" (milliampere-seconds). In an alternative embodiment, for each greyscale value a value for the high voltage is also stored in addition to the tube current-time product value. This is typically stored in units of "kV" (kilovolts). In alternative embodiments, additional acquisition parameters can be stored as well here. In this case, the calculation unit is expanded so that it determines other, further acquisition parameters (for example a separate time duration of the radiation exposure/exposure time) in addition to the respective target greyscale values. In an alternative embodiment, the association table also includes at least one value for the tube current or for the tube current-time product for every calculated target greyscale value. Alternatively, a high-voltage value can also be additionally stored. The memory can be provided directly in the control unit. Alternatively, this can be an external memory that the control unit can access.

The control unit is designed to control the high-energy tomosynthesis scan with the data that it has read out from the association table of the memory. The data can relate to the tube current or the tube current-time product. In an expansion of the invention, the data also further relate to the high voltage. The control values (tube current time, high voltage) are respectively determined separately or individually for each projection angle. It is thus possible to select a different tube current-time product value and a different high-voltage value for the high-energy scan for the central beam than for the projection angles from +/−6°. This is based on the fact that different tissue structures that require different acquisition parameters (tube current time, high-voltage) are acquired from the different projection angles.

According to a preferred embodiment, the evaluation unit includes a reconstructor. The reconstructor is designed to reconstruct a volume image based on the acquired image data that have been acquired by means of the low-energy tomosynthesis scan. Alternatively, however, the reconstructor can also be activated as a separate module of the control unit. For example, the reconstructor can be designed in order to apply reconstruction methods. Filtered back projections (FBP) or iterative reconstruction algorithms (for example the maximum likelihood (ML) algorithm) can be used here. The reconstructor serves to provide a three-dimensional image data set that can be presented at a display unit and includes different greyscale values for the individual volume segments.

The calculation unit serves to calculate a respective target greyscale value for a volume segment in the second high-energy scan. According to the invention, the greyscale values of the volume segments of the low-energy scan that are relevant to the respective determined projection angles are taken into account for this. The size of the volume segment is configurable. This has the advantage that, initially, a larger volume segment (megavoxel segments) is considered so that the calculation unit can provide the result of the calculation as quickly as possible. Smaller volume segments can then be selected iteratively so that the result of the calculation unit is provided at a required resolution. What is known as a pixel binning method can thereby be applied to save time.

A number of advantages are achieved with the control unit according to the invention and with the control method according to the invention. Optimal acquisition parameters for the depiction of the contrast agent can thus respectively be set separately and with differentiation for a patient examination. The acquisition parameters are set on the basis of the data that have been determined by the preceding low-energy tomosynthesis scan. Furthermore, the image quality for the high-energy scan can be improved, while at the same time the x-ray radiation dose for the patient can be kept as low as possible. Overall, the finding quality can be improved in that a better precision and significance of the achieved image data can be ensured. The acquisition parameters (in particular the tube current-time product value, but also the high-voltage parameter and possibly other acquisition parameters) can respectively be selected specifically and differently from patient to patient and be automatically adapted to the respective examination conditions and determined. Moreover, a projection angle-specific and/or examination-specific adjustment of the acquisition parameters can also be determined that can possibly deviate from one another from a first examination to a second examination of the same patient.

The tomosynthesis method is typically based on a three-dimensional data set so that different projection slices are recombined into a three-dimensional data volume. It is likewise possible to depict four-dimensional data sets, for instance if an animated presentation of the contrast agent progression over time should be shown. In a simpler embodiment, the proposal according to the invention can also be applied to two-dimensional data sets.

The type of finding or the intended medical use is not limited. In addition to a mammography, for example, the method can also be used to diagnose lung cancer or cardiac illnesses. Depending on the embodiment of the present invention, different acquisition parameters are determined for the second, high-energy tomosynthesis scan. In a first embodiment, only a tube current-time product value is determined. In a second embodiment, in addition to the tube current-time product value the value for the high voltage is also determined. Additional embodiments relate to the determination of other acquisition parameters.

The above object also is achieved by a control method according to the invention. It is thereby provided that a low-energy tomosynthesis scan is initially acquired that is subsequently evaluated in order to determine a greyscale value for the volume segments for every projection slice and for every angle.

After implementing the low-energy tomosynthesis scan, the respective corresponding projection angles are determined at which the high-energy tomosynthesis scan should also be executed. Here the same projection angles are typically used in the same order or in the reverse order. Alternatively, only a selection of the projection angles can be determined.

Target greyscale values for the respective projection angles determined in the preceding can subsequently be calculated. The determined greyscale values of the low-energy tomosynthesis scan enter into this calculation. Only the voxels or volume segments relevant to the respective projection angles are taken into account for this. The relevant volume segments are those that are located in the beam or fan region of the respective projection angle. This takes place with access to a mapping table in which a tube current-time product value (and if necessary a high-voltage value) are stored for each greyscale value and/or target greyscale value. The high-energy tomosynthesis scan is then controlled with these read-out values.

The method according to the invention is typically divided into three time segments: in a first low-energy segment, the low-energy tomosynthesis acquisition is executed. In a second calculation segment, the low-energy exposure is evaluated with regard to the greyscale values. In a third time segment, the high-energy tomosynthesis scan is controlled and executed using the determined greyscale values from the low-energy scan.

An alternative, simpler achievement of the object is provided by a calculation unit that can be used to control a high-energy scan or that can be connected upstream of a control unit described in the preceding. The calculation unit also serves to control the high-energy tomosynthesis scan with regard to the tube current-time product and/or with regard to the high voltage (in addition to the evaluation of the low-energy image data) in that a high-energy target greyscale value is determined for each volume segment of the examination subject in order to compare said high-energy target greyscale value with the respective corresponding low-energy tomosynthesis scan. Based on this greyscale value comparison that is respectively—iteratively—implemented for all (corresponding) col segments, an attenuation coefficient for determination of a subject density (in particular breast density) can then be derived and associated with this. In one version, a breast density profile can also be subsequently created and displayed. With access to the association table, for each calculated target greyscale value the respective value for tube current/high voltage that serves to control the high-energy tomosynthesis scan can be determined.

The above object also is achieved in accordance with the present invention by a non-transitory, computer-readable data storage medium encoded with programming instructions that, when the storage medium is loaded into a computerized control and evaluation system of a tomosynthesis apparatus, cause the control and evaluation system to operate the tomosynthesis apparatus according to one or more of the above-described embodiments.

BRIEF DESCRIPTION OF THE DRAWINGS

FIG. 4 is a flowchart of the method according to the invention according to a preferred embodiment.

DESCRIPTION OF THE PREFERRED EMBODIMENTS

In the following the invention is explained in detail in connection with exemplary embodiments that are presented in the figures.

Figure 3:
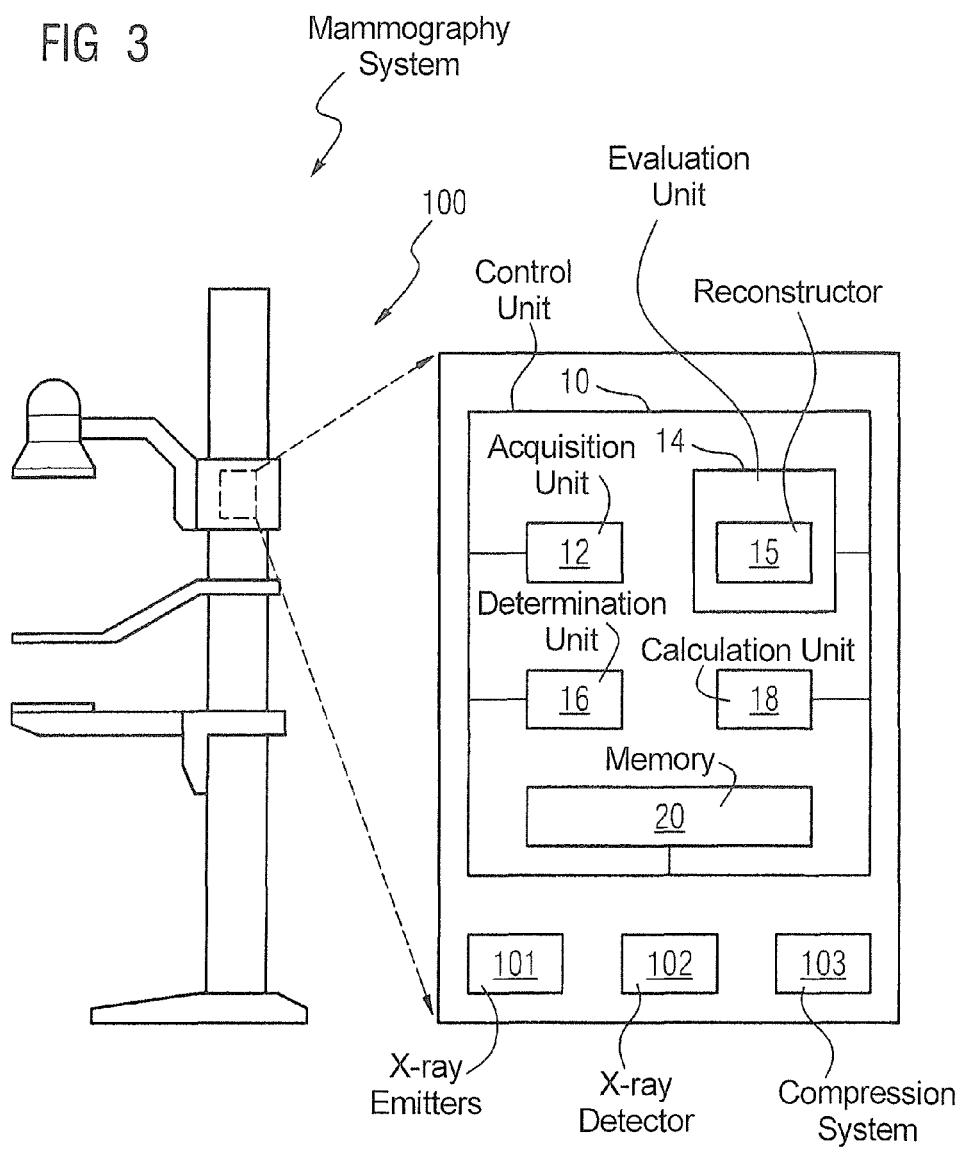
FIG. 3 is an overview presentation of a mammography system with a control unit according to the invention, according to a preferred embodiment.

The basic design of a mammography system 100 with the modules according to the invention, according to a preferred embodiment, is explained in detail with reference to FIG. 3. The mammography system 100 has a control unit 10. As is schematically indicated in FIG. 3, the control unit 10 can be designed as an embedded system in the mammography system 100 or in associated computer-based instances. The mammography system has a modality for acquisition of image data (in particular an x-ray system) comprising x-ray source 101, x-ray detector 102 and compression system 103. Depending on the embodiment, the mammography system 100 can also have additional components, for example the mounts, one or more acquisition workstations, user interfaces (keyboard, mouse, monitor), corresponding data lines and interfaces that are not shown in FIG. 3 for the purposes of clarity. The control unit 10 is engaged in data exchange with electronic modules of the mammography system 100, in particular with the x-ray sources 101 (here mobile x-ray sources are provided), with the x-ray detector 102 and/or with the compression system 103.

The control unit 10 includes multiple electronic modules that are engaged in data exchange with one another via a bus system or a network. In one embodiment, the control unit 10 comprises an acquisition unit 12, an evaluation unit 14 (that for its part comprises a reconstructor 15), a determination unit 16, a calculation unit 18 and a memory 20. In alternative embodiments, additional modules and/or computer-based instances are provided here in order to be able to show the control result of the control unit 10 in an accelerated manner. For example, an additional memory unit and particular arithmetic logic units or, respectively, (mathematical) coprocessors can be provided for this.

In principle, the control unit 10 serves to control a dual-energy tomosynthesis scan that is driven with two different energy levels. The control unit 10 thereby serves to determine the acquisition parameters for the subsequent tomosynthesis scan. The parameter determination of the control unit 10 takes place on the basis of an evaluation of the information and image data that have been determined by the first tomosynthesis scan. In particular, the determination by the control unit 10 is based on image data of the low-energy tomosynthesis scan. The image data are represented as greyscale values with a greyscale value distribution over the examined and radioscoped scans. The first tomosynthesis scan, which is implemented with a low energy level driving the x-ray source, serves to acquire morphological structures of the examination subject. These are a tissue composition, regions of tissues of different density, microcalcifications, or other tissue information. Moreover, surgical objects (for example implants or the like) can also be acquired and shown in this first tomosynthesis scan. The first tomosynthesis scan occurs from different projection angles. It is typically for the x-ray source 101 to be pivoted in a range of +/−25°. The pivot plane is parallel to a longitudinal axis of the body of the patient. These different structures lead to different greyscale values of the acquired image data of the first tomosynthesis scan.

The acquisition unit 12 serves to acquire the data that have been acquired by means of the low-energy tomosynthesis scan. The acquisition unit 12 is engaged in data exchange with the acquisition workstation of the mammography system 100.

The evaluation unit 14 serves to evaluate the image data acquired by means of the acquisition unit 12. The evaluation unit 14 evaluates the greyscale values of the examined volume. For this purpose, the examined volume is divided into a series of slices (projection slices). Each projection slice comprises a plurality of volume segments.

Figure 1:
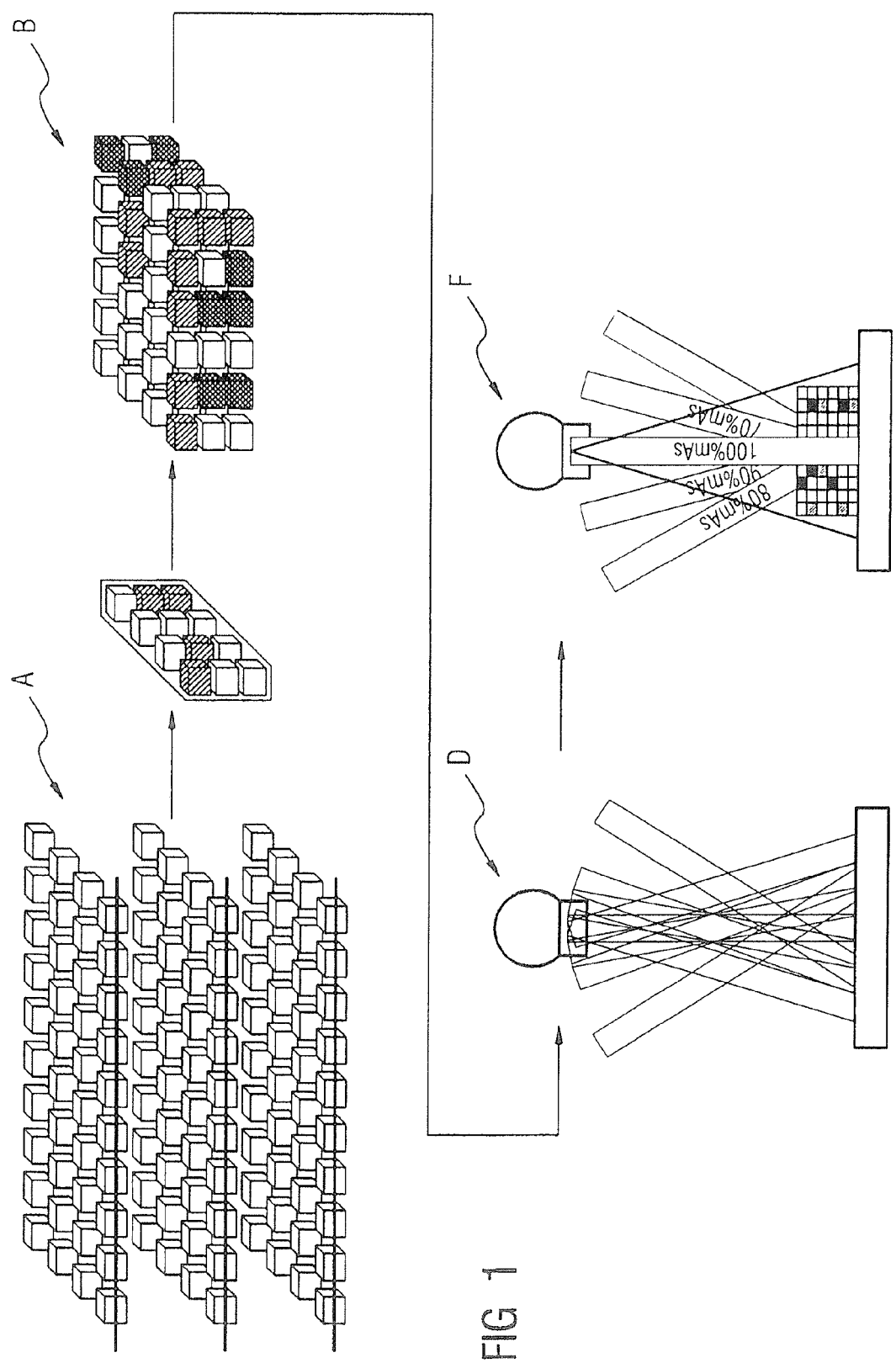
FIG. 1 schematically illustrates steps implemented by the control unit according to the invention according to a preferred embodiment of the invention.

The preceding calculation process to control the second tomosynthesis scan is shown in detail in FIG. 1. On the left side of FIG. 1, the three-dimensional examination subject is presented as a principle presentation for the low-energy volume. It comprises slices 1, 2, 3. In order to clarify that the image data of the low-energy tomosynthesis scan are acquired by the acquisition unit 12 in Step A, a reference character for the basic workflow of a control method according to the invention (which is explained in detail in the following with reference to FIG. 4) is found at the respective work or calculation steps in FIG. 1. After breakdown of the volume to be examined into individual volume segments, for each volume segment the greyscale value can be determined from the first tomosynthesis scan. What is known as a "density profile" can also be derived from this. Alternatively, here as well additional statistical variables can be calculated, for example a signal-to-noise ratio (SNR), a mean value and additional image-related data. Those volume segments are thereupon determined that are located within a fan region of the respective (defined) angle. Depending on at what angle the x-ray source 101 exposes the examination subject before the x-ray radiation attenuated by the exposed tissue has been acquired by the x-ray detector 102, different volume segments are acquired by the x-ray radiation. These relevant volume segments are determined for each defined projection angle. Different relevant volume segments with greyscale values or, respectively, greyscale value distributions that are different in part thereby result for different projection angles. The calculation unit 18 now serves to calculate a target greyscale value for a respective defined projection angle. In other words, a different target greyscale value is normally determined for the central beam (that strikes the x-ray detector 102 at an angle of 90° from the x-ray source 101) than for the projection angle (that strikes the detector 102 at an angle of +/−25°). All greyscale values of those volume segments (the relevant volume segments) that are located in the beam region of the respective projection angle in the examination subject are taken into account in the calculation of the target greyscale value for a respective, specific projection angle.

According to the invention, an association table in which a tube current-time product value is saved with regard to each target greyscale value is stored in the memory 20. In one development of the invention, the association or mapping table can also comprise additional entries for the respective greyscale values. For example, in addition to the tube current-time product value a value for the high voltage (in kilovolts) can also be stored with regard to each target greyscale value.

In a preferred embodiment, the calculation unit 18 directly accesses the memory 20 to read out the tube current-time product value and/or the high-voltage value for the respective projection angle.

The calculation unit 18 can be operated in different variants.

In a first variant, all greyscale values of all volume segments that are located in the radiation region of the respective projection angle are determined. According to a first variant, the target greyscale value is derived that is determined from a maximum of the greyscale values of all volume segments. This maximum greyscale value is then used for the determination of the tube current-time product value (via access to the mapping table in memory 20). In a second variant, the target greyscale value is determined with which a constant contrast/noise ratio can be determined for all participating volume segments. According to a third variant, a statistical mean value is determined for all greyscale values of all participating volume segments. This mean value is used in order to calculate the tube current-time product value from the association table. Alternative embodiments here relate to a combination of the variants mentioned in the preceding.

Figure 2:
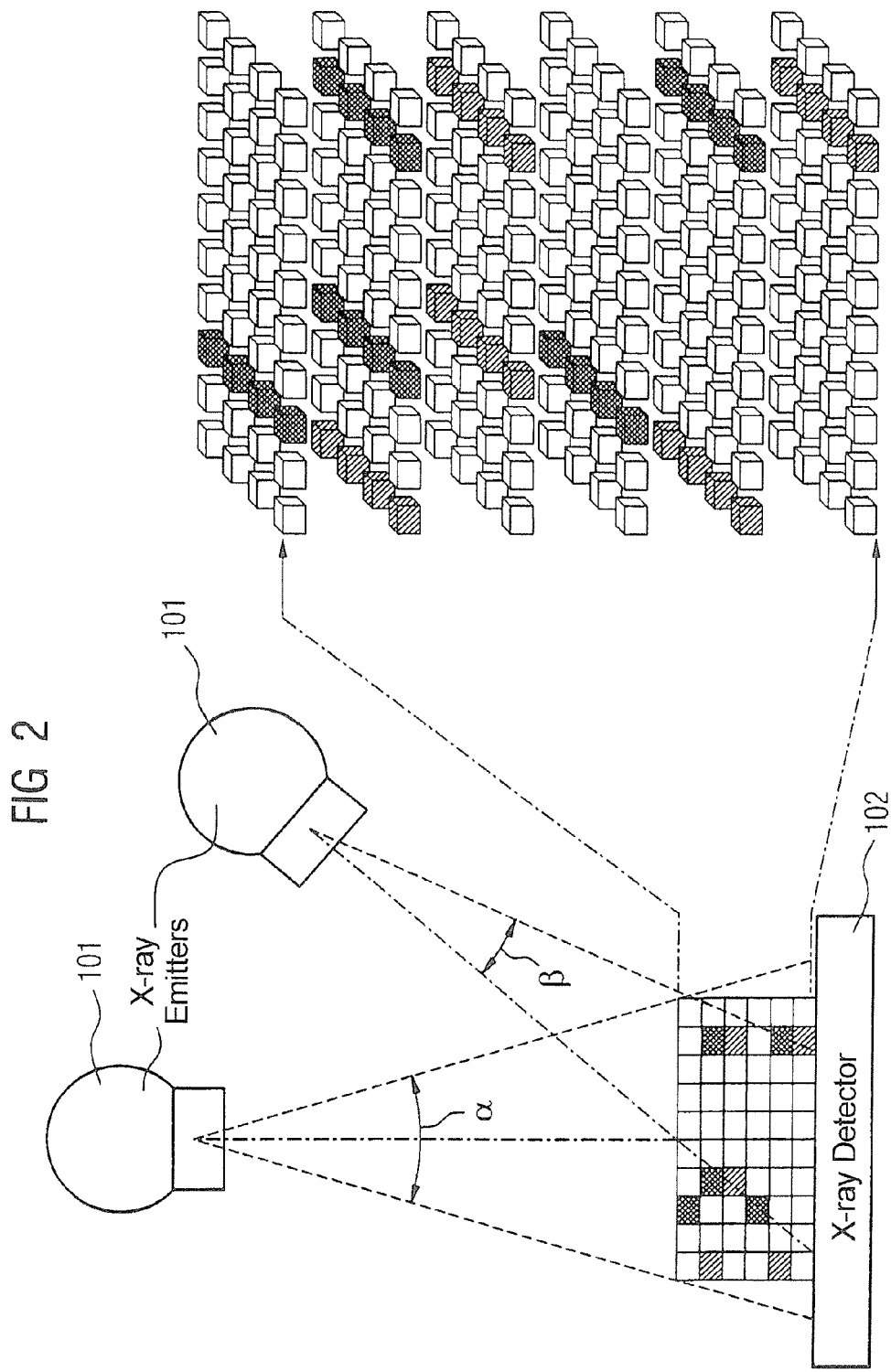
FIG. 2 is a schematic representation of an exposed tissue region for two different projection angles.

FIG. 2 concerns a principle representation of the control method according to the invention. As depicted in FIG. 2, the x-ray emitters 101 are pivoted into different positions so that they strike the x-ray detector 12 with a different projection angle α, β. The subject to be examined is represented in FIG. 2 as a rasterized cuboid that is borne across the detector 102. The examination volume comprises individual volume segments in different projection slices. The volume segments that are differently marked in FIG. 2 (different hatching) should identify different tissue structures. For example, the narrow or, respectively, strong hatching should thus identify dense tissue segments, while light regions should represent normal tissue. In FIG. 2, the left, upper x-ray emitter 101 exposes the examination subject with a radiation angle α. In the example shown in FIG. 2, a middle beam orthogonally strikes the x-ray detector 102. In contrast to this, the right, lower emitter 101 exposes the examination tissue at a projection angle β and strikes the x-ray detector 102 at a different angle (at an angle of approximately 45° in the example of FIG. 2). From FIG. 2 it is clear that different volume segments of the volume to be examined are exposed depending on the respective projection angle. These respective volume segments that are exposed for a specific projection angle are determined by the calculation unit 18. Therefore, the volume segments calculated as relevant are specific to the projection angle. For each individual volume segment, the determined greyscale values are reconstructed in order to derive a target greyscale value. This method is executed iteratively for all projection angles, and likewise iteratively (in a second iteration) for all volume segments of the respective projection angle. The relevant volume segments of the examination subject that is located in the fan region of a projection angle α and whose greyscale value is reconstructed should be emphasized on the right side of FIG. 2. By accessing the mapping table of the memory 20, using the determined total signal value over the respective exposed examination region (with the respective volume segments) the respective values for the tube current or for the tube current-time and for the high voltage can subsequently be determined in milliampere-seconds and kilovolts for each respective projection angle of the subsequent second tomosynthesis acquisition. Tube current (and facultatively high voltage) are thereby respectively calculated separately and independently for each projection angle of the subsequent high-energy acquisition.

In the following, a workflow according to a preferred embodiment of the control method according to the invention is explained in detail with reference to FIG. 4. Individual method steps can thereby also be applied in a modified order.

In Step A the image data of a first tomosynthesis scan are acquired after starting the control system. This takes place with access to the mammography system 100. It is thereby advantageously a tomosynthesis scan with a low energy level (low-energy).

In Step B the acquired image data are evaluated in order to determine a greyscale value for each volume segment. This evaluation takes place in cooperation with Step C.

In Step C a projection angle is respectively determined at which the second tomosynthesis scan (in particular the high-energy scan) should be executed or the low-energy scan has been executed.

The evaluation unit 14—or alternatively also the calculation unit 18—can thereupon determine all greyscale values of all of those volume segments that are located within the fan region for the respective determined projection angle α, β. After all greyscale values of the participating volume segments have been determined, according to different variants that have already been described above a target greyscale value can be determined for each projection angle. This takes place in Step D.

As shown in FIG. 4, in one variant it is possible to again produce an additional angle determination here in order to determine different angles or additional angles, for example, based on which a new calculation is then implemented.

An access to the memory 20 in order to derive a tube current-time product value regarding each greyscale value takes place in Step D. Here different variants are likewise provided again. In a first variant it is thus possible that a tube current-time product value (and facultatively another value for the high voltage) is (are) stored in the association table regarding each greyscale value. In a second variant, it is possible that a tube current-time product value is stored only with regard to a determined target greyscale value. The second variant has the advantage that the memory 20 with the target greyscale value must only be accessed once in order to determine the tube current for each projection angle individually. In Variant 1, the memory 20 must be accessed for all participating volume segments. The respective result of the access must be stored in a buffer memory. A mean value or other statistical method [sic] the values stored in the buffer method can subsequently be derived for the tube current as a final result of the control method.

In Step F the second tomosynthesis scan is then controlled with the determined values for the tube current—and facultatively for the high voltage—for each individual projection angle.

The method then ends.

In a variant of the invention, the recursion after Step D going back to before Step C can also be omitted.

A significant advantage of the control method according to the invention is apparent in that the acquisition parameters—in particular the values for the tube current or the tube current-time product specifically for every patient, in particular for each examination specifically, and for each projection angle—are calculated individually and independently of one another. Given an improved image quality, the radiation exposure for the patient can be reduced. This leads overall to a better tomosynthesis result.

In summary, the invention can be described as follows:

A control method for a dual-energy tomosynthesis is proposed that can be implemented in a control unit 10. The control method evaluates the image data—in particular the greyscale values—of a first tomosynthesis scan in order to derive a value for a tube current or a tube current-time product from the determined greyscale values with access to a mapping table. This is used as a result and as a control signal for activation of the s second tomosynthesis scan, which is typically driven at a high energy level. The tube current that is calculated in such a manner is thereby executed individually (thus independently of one another) and separately for every single projection angle and for every examination.

Although modifications and changes may be suggested by those skilled in the art, it is the intention of the inventor to embody within the patent warranted hereon all changes and modifications as reasonably and properly come within the scope of his contribution to the art.

I claim as my invention:

1. A control unit to control a high-energy tomosynthesis scan in a contrast agent-assisted dual-energy tomosynthesis of an examination subject, said control unit comprising:
   an acquisition unit configured to acquire image data from at least one low-energy tomosynthesis scan of an examination subject;
   an evaluation unit supplied with said image data and configured to automatically evaluate said image data to identify a grayscale value for each volume segment of the examination subject represented in said image data;
   a determination unit configured to determine at least one projection angle at which the low-energy tomosynthesis scan was implemented and the high-energy tomosynthesis scan is to be implemented;
   a calculation unit configured to calculate, for each projection angle determined by the determination unit, a target grayscale value based on all grayscale values for all volume segments represented by said image data that fall within a radiation region of the respective projection angle;
   said calculation unit being configured to access a memory in which an association table is stored, said association table comprising at least one operating parameter, selected from the group consisting of a tube current-time product value, and a high voltage value, respectively associated with different stored grayscale values, to identify one of said stored grayscale values that corresponds to the target grayscale value, and to select said at least one operating parameter from the association table that is respectively associated with said one of said stored grayscale values as a selected at least one operating parameter that will produce said target grayscale value in said high-enemy tomosynthesis scan for each projection angle determined by said determination unit; and
   said calculation unit being configured to operate said acquisition unit to implement said high-energy tomosynthesis scan using said selected at least one operating parameter for each projection angle determined by said determination unit selected from said table.

2. A control unit as claimed in claim 1 wherein said calculation unit is configured to calculate said target grayscale value for each projection to produce a constant contrast to noise ratio from projection-to-projection.

3. A control unit as claimed in claim 1 wherein said calculation unit is configured to calculate said target grayscale value for each projection to produce a constant signal mean value from projection-to-projection.

4. A control unit as claimed in claim 1 wherein said evaluation unit comprises a reconstructor configured to reconstruct a volume image from the acquired image data of the low-energy tomosynthesis scan.

5. A control unit as claimed in claim 4 wherein said reconstructor is configured to reconstruct said volume image by implementing a reconstruction algorithm selected from the group consisting of a filtered back projection algorithm and an iterative reconstruction algorithm.

6. A control unit as claimed in claim 1 wherein said calculation unit is configured to implement an iterative calculation procedure for said volume segments in respective descending size and to provide a calculation result after a configurable period of time.

7. A control unit as claimed in claim 1 wherein said calculation unit is configured to generate said target grayscale value for each projection by generating a target grayscale value for each volume segment of the examination subject that is relevant for the respective projection angle, and to compare the respective, determined target grayscale values with the corresponding, respective grayscale values of the low-energy tomosynthesis scan represented by said image data in order to determine a subject density, and to use said subject density, together with said association table, to select said at least one operating parameter.

8. A method to control a high-energy tomosynthesis scan in a contrast agent-assisted dual-energy tomosynthesis of an examination subject, comprising:
   operating an acquisition unit acquire image data from an examination subject with at least one low-energy tomosynthesis scan;
   in a processor arrangement, automatically evaluating the acquired image data to determine, for each volume segment of the examination subject represented by said image data, a grayscale value;
   in said processing arrangement, determining at least one projection angle at which the low-energy tomosynthesis scan has been executed and at which the high-energy tomosynthesis scan will be executed;
   in said processing arrangement, automatically calculating, for each determined projection angle, a target grayscale value using all of the determined grayscale values for all of the volume segments that fall within a radiation beam region for the respective projection angle;
   access a memory in which an association table is stored in which at least one operating parameter, selected from the group consisting of a tube current-time product and a high voltage value, is respectively associated with different stored grayscale, values, to identify one of said stored grayscale values that corresponds to the target grayscale value, and selecting at least one operating parameter from said table from the association table that is respectively associated with said one of said stored grayscale values as a selected at least one operating parameter that will produce said target grayscale value in said high-energy tomosynthesis scan for each determined projection angle; and automatically operating said acquisition unit in a high-energy tomosynthesis scan of the examination subject using the selected operating value obtained from said memory for each determined projection angle in said high-energy tomosynthesis scan.

9. A non-transitory, computer-readable data storage medium encoded with programming instructions, said storage medium being loaded into a control and evaluation processor of a mammography apparatus, said mammography apparatus comprising an image data acquisition unit, and said programming instructions causing said control and evaluation processor to:

receive image data acquired by said image acquisition unit in at least one low-energy tomosynthesis scan of an examination subject;

evaluate the acquired image data in order to determine a grayscale value for each volume of the examination subject represented by said image data;

determine at least one projection angle at which the low-energy tomosynthesis scan was executed and at which a high-energy tomosynthesis scan of the examination subject is to be executed;

calculate, for each projection angle, a target grayscale value from all of the determined grayscale values for all of the volume segments of the examination subject that fall within a radiation beam region of the respective projection angle;

access a memory in which an association table is stored, in which at least one operating parameter selected from the group consisting of a tube current-time product value, and a high voltage value, is respectively associated with different stored grayscale values, identify one of said stored grayscale values that corresponds to the target qrayscale value, and selecting at least one of said operating parameters from said association table that is respectively associated with said one of said stored qrayscale values as a selected at least one operating parameter that will produce said target qrayscale value in said high-enemy tomosynthesis scan for each determined projection angle; and operate said image data acquisition unit to conduct said high-energy tomosynthesis scan of the examination subject with said selected at least one operating value for for each determined projection angle.

\* \* \* \* \*